US007592148B1

(12) United States Patent
Yamanouchi et al.

(10) Patent No.: US 7,592,148 B1
(45) Date of Patent: Sep. 22, 2009

(54) METHOD FOR EXAMINING HUMAN KIDNEY DISEASE BY DETECTING THE FATTY ACID BINDING PROTEIN

(75) Inventors: Masaya Yamanouchi, Kusatsu (JP); Akiko Honda, Toyonaka (JP); Hiromi Hase, Tokyo-to (JP); Takeshi Sugaya, Itami (JP); Kenjiro Kimura, Tokyo-to (JP)

(73) Assignee: CMIC Co., Ltd., Tokyo (JP)

( * ) Notice: Subject to any disclaimer, the term of this patent is extended or adjusted under 35 U.S.C. 154(b) by 899 days.

(21) Appl. No.: 09/578,693

(22) Filed: Jul. 26, 2000

Related U.S. Application Data

(63) Continuation-in-part of application No. PCT/JP98/05319, filed on Nov. 26, 1998.

(30) Foreign Application Priority Data

Nov. 26, 1997 (JP) .................................. 9-323684

(51) Int. Cl.
*G01N 33/53* (2006.01)
*G01N 33/566* (2006.01)

(52) U.S. Cl. .................. 435/7.21; 435/7.1; 435/7.8; 436/501; 436/518

(58) Field of Classification Search .................. 435/4, 435/5, 7, 8, 12, 188, 184, 810, 69.1, 240.27, 435/70.21, 172.3, 172.2, 325, 7.1, 7.21, 7.8; 424/8, 12, 145.1, 152.1, 545, 130.1, 809; 23/230 B; 514/2, 12–17; 436/501, 518, 436/536, 537, 543, 546, 73, 172, 175, 824, 436/825, 820
See application file for complete search history.

(56) References Cited

U.S. PATENT DOCUMENTS 4,281,061 A * 7/1981 Zuk et al. .................... 435/7

FOREIGN PATENT DOCUMENTS

| JP | 02-275359 | 9/1990 |
| JP | 431762 A | 2/1992 |
| JP | 05333025 | 12/1993 |
| WO | WO 9308276 | 4/1993 |

OTHER PUBLICATIONS

Kimura et al., Primary structure and cellular distribution of two fatty acid-binding proteins in adult rat kidneys, The Journal of Biological Chemistry, vol. 266., No. 9, pp. 5963-5972, Mar. 25, 1991.*
Olson et al., A comparison of male rat and human urinary proteins: Implications for human resistance to hyaline droplet nephropathy, Toxicology and Applied Pharmacology, vol. 102, pp. 524-536, 1990.*
Galaske et al., Plasma protein handling in the rat kidney: Micropuncture experiments in the acute heterologous phase of anti-GBM-nephritis., Pflugers Archives of European Journal of Physiology., vol. 375., No. 3, pp. 269-277, 1978, Abstract Only.*
Nagasawa., Interaction of concanavalin A and GBM glycoprotein in vivo., Japan Medical Research Foundation Publication., vol. 7(Glomerulonephritis), 1979, pp. 39-51, Abstract Only.*
Gorski et al., Increased Fatty Acid-Binding Protein Concentration in Plasma of Patients with Chronic Renal Failure, Clinical Chemistry 43, No. 1, 1997, pp. 193-195.*
Simon et al. "Suppressor and Activator Functions mediated by a repeated heptad sequence in the Liver Fatty acid-binding protein gene." The Journal of Biological Chemistry, vol. 272, No. 16, Apr. 18, 1997, pp. 10652-10663.*
Uchida et al., FEBS Letters 357, pp. 165-167, 1995.
Saito et al., Toxicology, 79, pp. 173-183, 1991.
J. Gorski et al., Clinical Chemistry, vol. 43, No. 1, pp. 193a-195 Jan. 1997.
W. A. Kaptein et al., Journal of Immunological Methods, vol. 217, pp. 103-111 (1998).
Y. Ohkaru et al., Journal of Immunological Methods, vol. 178, pp. 99-111 (1995).
Maatman et al., Biochem. J., 288, p. 285-290, 1992 "Molecular identification of the liver- and the heart-type fatty acid-binding proteins in human and rat kidney".
Pervaiz, Syed et al., FJ Res. Comm., "Homology and structure-function correlations between $\alpha_1$-acid glycoprotein and serum retinol-binding protein and its relatives"; pp. 209-214; May 14, 1987.
Veerkamp et al., Prog. Lipid Res., vol. 34, No. 1, pp. 17-52, 1995 "Cytoplasmic fatty acid-binding proteins: their structure and genes".
Maatman, Ronald et al., Biochem. J. (1991), vol. 273, pp. 759-766 "Two Types of fatty acid-binding protein in human kidney".
Kimura et al., FEBS Letters, vol. 246, No. 1,2, pp. 101-104 (1989) "Kidney fatty acid-binding protein: identification as $\alpha_{2U}$-globulin".
Lowe et al., J. Biol.Chem., vol. 260, No. 6, pp. 3413-3417 (1985) "Human Liver Fatty Acid Binding Protein".
Kanda et al., Gastroenterology, vol. 110, pp. 339-343 (1996) "Intestinal Fatty Acid-Binding Protein is a Useful Diagnostic Maker for Mesenteric Infarction in Humans".

(Continued)

*Primary Examiner*—Lisa V Cook
(74) *Attorney, Agent, or Firm*—Birch, Stewart, Kolasch & Birch, LLP

(57) ABSTRACT

Method for examining kidney disease, which comprises detecting fatty acid binding protein derived from kidney tissues, which is present in specimen collected from mammal excluding Rodents. By the present method, it is possible to obtain test results, which may be very important information for diagnosis or prognosis of kidney disease that has been very difficult in the past. Based on test results obtained by the present method, it may be possible to select a suitable method for treatment of kidney disease with taking into consideration risks such as the prognosis, etc. Besides, the present method can be applied to, in addition to the kidney disease samples, urine samples as well, so that the examination procedure can be simple and efficient.

13 Claims, 4 Drawing Sheets

(4 of 4 Drawing Sheet(s) Filed in Color)

OTHER PUBLICATIONS

English Abstract of The Gist of the 47th Large Bowel Cancer Seminar, p. 42, 1997.
Yamazaki et al., J.Surg.Oncol., 72:83-87, (1999)—Abstract.
Fuji et al., Domyakukoka, vol. 24, pp. 353-361, 1996 (Abstract).
Drickamer et al., J. Biol. Chem., vol. 256, pp. 3634-3636, 1981.
Unterman et al., Proc. Natl. Acad. Sci. USA, vol. 78, pp. 3478-3482, 1981.
Lam et al., J. Biol. Chem., vol. 263, pp. 15762-15768, 1988.
Genbank accession No. M10617.
Genbank accession No. J00737.
Wodzig et al. Ann. Clin. Biochem., vol. 34, pp. 263-268, 1997.
Van Nieuwenhoven et al., Lipids, vol. 31 Suppl., pp. S223-S227, 1996.

* cited by examiner

METHOD FOR EXAMINING HUMAN KIDNEY DISEASE BY DETECTING THE FATTY ACID BINDING PROTEIN

This application is a continuation-in-part application of PCT International Application No. PCT/JP98/05319 which has an international filing date of Nov. 26, 1998 which designated the United States, and which claims priority to Japanese Application 9-323684/1997, which has a Japanese filing date of Nov. 26, 1997 the entire contents of which are incorporated by reference.

TECHNICAL FIELD

The present invention relates to a method for examination for diagnosing the prognosis, etc. of kidney diseases.

BACKGROUND ART

Kidney diseases such as chronic nephritis usually show complicated and various symptoms, and for such kidney diseases, it is important to apply a suitable treatment thereto as early as possible so that a transition into chronic renal insufficiency, which requires dialysis treatment, can be avoided, or can be delayed as long as possible. In case of the transition from the initial stage of kidney diseases into chronic renal insufficiency, it is said that it is important to find, as check points for determining the prognosis inclemency, a continuous high proteinuria or hypertension from a clinical view point, or recently interstitial fibrosis as well as glomerulosclerosis from a histological view point. However, no decisive method has actually been established yet for accurate diagnosis of the prognosis of kidney diseases, and it has been desired to develop a useful method for diagnosis and for examination.

On the other hand, fatty acid binding protein (FABP) is known to be a group of proteins of a molecular weight of about 15 kilodalton, existing in cytosol, and having an ability of binding to a fatty acid. The physiological functions of these proteins are considered to participate in the regulation of metabolic enzyme systems by transfer or accumulation of fatty acid within the cells, but the detailed physiological activities of these proteins have not been clarified yet. There have been known at least seven molecules of FABP such as liver-type (L-FABP), intestine-type (I-FABP), heart muscle-type (H-FABP), brain-type (B-FABP), cutaneous/epidermal-type (C-FABP/E-FABP), fat cell-type (aP2), peripheral neuron-type (myelin-P2), etc., and the primary structures thereof have been determined. All of these FABPs show an ability of binding to a fatty acid, and some of them have a common region wherein a sequence has been duly preserved, so that it is considered that they are a family developed from the common ancestor genes. However, each FABP has a different primary structure, and shows a unique histologic distribution pattern. The nomenclature of FABP means in which organ such FABP is firstly found, but does not mean that such FABP exclusively exists in such organs.

Aiming at FABP, the following diagnostic methods have been known. JP-4-31762-A discloses that the level of H-FABP derived from human heart muscle in serum or urine can be quantitatively assayed by immunoassay using an antibody in order to diagnose myocardial infarction. WO 93/08276 and Kanda et al., Gastroenterology, vol. 110, p. 339-343, 1996 disclose that since the I-FABP level in serum is extremely increased during the small intestine ischemia, etc., I-FABP may be a useful diagnosis marker for intestine diseases. However, they do not have any relation with kidney diseases, and they are concerned with the detection of FABP as an indicator, which leaks accompanied by tissue injury during ischemia, but they never aim at the existence thereof in the tissues.

Recently, YAMAZAKI et al. reported that the existence of L-FABP in large bowel cancer or metastasized lesion thereof is concerned with the malignancy or prognosis of cancer, and the higher the existing amount of L-FABP is, the better the prognosis is (the Gist of the 47th Large Bowel Cancer Seminar, p. 42, 1997). However, this is a finding for a specific tissue such as large bowel cancer.

Moreover, kidney-type FABP existing at male rat kidney has been known to be derived from $\alpha_{2u}$-globulin, and JP-5-333025-A discloses that the increase in urinary $\alpha_{2u}$-globulin level can be determined in order to diagnose the $\alpha_{2u}$-globulin nephropathy which is caused in male rats by the administration of chemical substances. However, it is a mere method for a specific nephropathy model, wherein $\alpha_{2u}$-globulin remarkably accumulates.

As mentioned above, no method for diagnosis or examination utilizing a relation between FABP in kidney tissues and kidney has been known.

DISCLOSURE OF INVENTION

An object of the present invention is to provide a method for examination, which is useful in diagnosing kidney diseases. The present inventors have studied on fatty acid binding proteins being derived from kidney tissues, and have originally found that there is a relation between the existence of fatty acid binding proteins in kidney tissue and the prognosis of kidney diseases, and finally have accomplished the present invention.

That is, the present invention relates to a method for examining kidney disease, which comprises detecting a fatty acid binding protein contained in a specimen collected from a mammal other than rodents, said fatty acid binding protein being derived from kidney tissue.

Another object of the present invention is to provide a method for examining kidney disease in rodent other than $\alpha_{2u}$-globulin nephropathy, which comprises detecting $\alpha_{2u}$-globulin (named also as Major Urinary Protein) or a fatty acid binding protein contained in a specimen collected from a rodent selected from rat and mouse, and determining the degree of decrease thereof as compared with that in a specimen collected from a normal animal, said fatty acid binding protein being derived from kidney tissue.

Further object of the present invention is to provide a reagent or kit for examination, which can be used in the present method for examination.

The mammals other than rodents, to which the present method can be applied, are, for example, humans, and further rabbits, apes, dogs, cats, cows, horses, sheep, goats, pigs, etc. Among these animals, the present method can preferably be applied to humans, rabbits and pigs, especially to humans.

The kidney diseases, to which the present invention can be applied, are not limited, but include, for example, diabetic nephropathy, glomerulonephritis, nephrotic syndrome, focal glomerulosclerosis, immune complex nephropathy (IgA nephropathy, membranous nephropathy, etc.), lupus nephritis, drug-induced renal injury, renal insufficiency and kidney graft rejection, etc.

It has been reported that in human kidney tissues, at least two fatty acid binding proteins are expressed, and one of them is liver-type one, and another one is heart muscle-type one (Maatman et al., Biochemical Journal, vol. 288, p. 285-290, 1992). Besides, among these fatty acid binding proteins, it is known that the liver-type fatty acid binding proteins distribute at the proximal tubule, and the heart muscle-type fatty acid binding proteins mainly distribute at the distal tubule (Maatman et al., Biochemical Journal, vol. 273, p. 759-766, 1991). In addition, the present inventors have found that these two kinds of fatty acid binding protein exist in rabbit kidney as well, as disclosed in Example 6 as mentioned below.

As mentioned above, in mammals other than rodents, fatty acid binding proteins (hereinafter, referred to as FABP) being derived from kidney tissues includes, for example, liver-type fatty acid binding protein (hereinafter, referred to as L-FABP) and heart muscle-type fatty acid binding protein (hereinafter, referred to as H-FABP).

Among them, L-FABP distributes at the proximal tubule, but according to the findings of the present inventors, the existence of the L-FABP is closely related with the prognosis of kidney diseases, and it is estimated that the more the L-FABP existing amount is, the better the prognosis is.

On the other hand, several kinds of FABP exist in rat kidneys, and one of them is H-FABP distributing at the distal tubule thereof. However, it has been clarified that another type of FABP called kidney-type FABP (K-FABP) is a molecule identical to $\alpha_{2U}$-globulin, which is known as an urinary main protein being specific to male rats, but 9 amino acid residues at the N-terminus thereof are deleted (cf. Kimura et al., FEBS Letters, vol. 246, p. 101-104, 1989). It is considered that the $\alpha_{2U}$-globulin is synthesized in the liver, released into the blood, and excreted into urine via the kidney, but most interestingly, some of $\alpha_{2U}$-globulins are reabsorbed into the renal tubule cells, and converted into kidney-type FABP by processing within the cells (Kimura et al, 1989). The present inventors have found that K-FABP distributes at the proximal tubule in male mice as well. In addition, a small amount of L-FABP exists at rat kidneys as well, but being different from human, L-FABP of rats exists more at the distal tubule than at the proximal tubule (Maatman et al., Biochemical Journal, vol. 288, p. 285-290, 1992).

As mentioned above, FABP being derived from kidney tissues of rodents (rats and mice) includes, for example, H-FABP, L-FABP and K-FABP. Among them, the present inventors have found that the existing amount of $\alpha_{2U}$-globulin or K-FABP derived therefrom is closely related with the prognosis of kidney diseases, and therefore, it is estimated that the more the existing amount thereof is, the better the prognosis of kidney diseases is. Accordingly, when the method for examination of the present invention is applied to rodents (rats and mice), a method for detecting $\alpha_{2U}$-globulin or K-FABP can be used therefor.

The specimens to which the present method is applied are, for example, kidney tissue, and further urine, blood (plasma or serum), extract from kidney tissue, etc. Among them, kidney tissue and urine are preferable specimens. More particularly, the preferable kidney tissue specimen is fragment sections of kidney tissues, which are collected by kidney biopsy, etc.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

BEST MODE FOR CARRYING OUT THE INVENTION

Figure 1A:
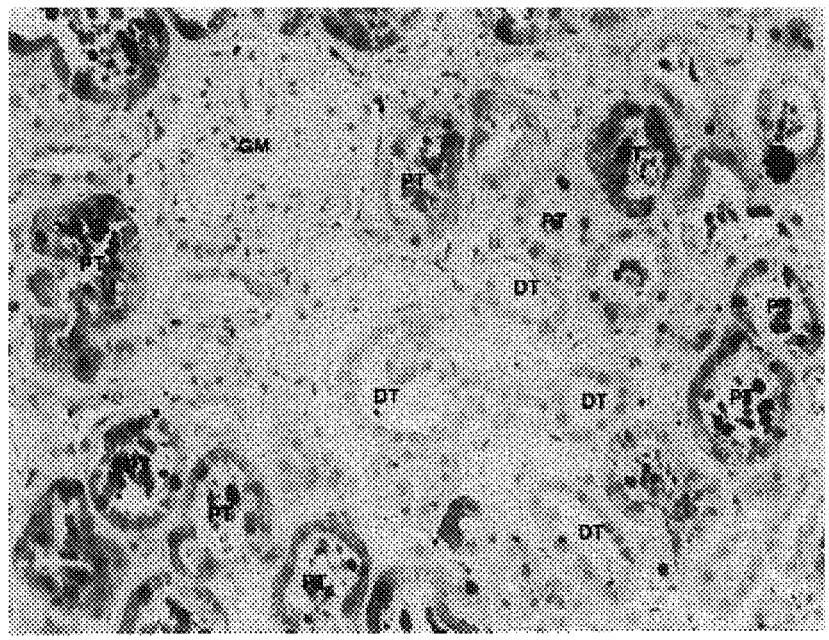
FIG. 1 is a photocopy of the tissue section, showing the result of immunostaining of FABP in normal human kidney tissues. Drawing A shows the result of staining by anti-L-FABP antibody, and Drawing B shows the result of staining by anti-H-FABP antibody. In the drawings, PT, DT and GM mean the proximal tubule, the distal tubule, and the glomerulus, respectively.

The detection of FABP (or $\alpha_{2U}$-globulin) in specimens is preferably carried out by immunochemical assay using an antibody specifically binding thereto.

The antibody may be prepared by using, for example, a purified FABP (or $\alpha_{2U}$-globulin) as an antigen.

As to each molecule type of FABP, distribution organs, molecular weights and primary structures thereof are reported (Fujii et al., Domyakukoka (i.e., Arteriosclerosis), vol. 24, p. 353-361, 1996; Veerkamp and Maatman, Prog. Lipid Res., vol. 34, p. 17-52, 1995). Besides, those of $\alpha_{2U}$-globulin are also known (Drickamer et al., J. Biol. Chem., vol. 256, p. 3634-3636, 1981; Unterman et al., Proc. Natl. Acad. Sci. USA, vol. 78, p. 3478-3482, 1981). Accordingly, the purification thereof can be carried out based on the above information.

FABP can be isolated from the organ tissues, in which a desired molecule type of FABP is considered to distribute. For example, L-FABP can be isolated from liver or kidney, and H-FABP can be isolated from heart or kidney. $\alpha_{2U}$-globulin of rats or mice can be isolated from liver, blood or urine, and K-FABP can be isolated from kidney. The isolation thereof can be carried out according to the method disclosed in the literature (Kelvin et al., J. Biol. Chem., vol. 263, p. 15762-15768, 1988). That is, the excised organ is homogenized, and subjected to ultra-centrifugation, and the obtained cytoplasm fractions are separated by gel filtration and anion exchange chromatography, etc., and the fractions containing FABP are selected and isolated based on molecular weight or fatty acid binding activity as indicators. Further, the fractions thus obtained are further subjected to SDS-polyacrylamide gel electrophoresis for further purification or for confirmation that there is only one band. The amino acid compositions or the amino acid sequence at the N-terminus of the purified protein is determined, and the results thereof are compared with the amino acid compositions or amino acid sequence as reported, by which a desired molecule type of FABP is confirmed.

The fatty acid binding activity of FABP (or $\alpha_{2U}$-globulin) is easily assayed, for example, by using a fluorescent probe such as ANS (1-anilinonaphthalene-8-sulfonic acid) (manufactured by Polysciences, Inc.). The fluorescent probe increases its fluorescent intensity by binding to a highly hydrophobic region such as fatty acid binding site of FABP. For example, after ANS is added to a solution containing FABP and mixed, the fluorescence intensity (excitation wavelength: 372 nm; fluorescence wavelength: 480 nm) can be determined. In addition, the fatty acid binding activity of FABP (or $\alpha_{2U}$-globulin) is also determined using RI-labeled fatty acid (Kimura et al., FEBS Letters, vol. 246, p. 101-104, 1989).

Further, since L-FABP and H-FABP show a high homology between human, mouse, pig, cow and rat, and it is known that the homology is more than 90% at the amino acid level, it is possible to utilize, for example, a mouse L-FABP as an antigen for obtaining an antibody binding to human L-FABP. In this case, it is an advantage that the purification of antigen is easy.

FABP (or $\alpha_{2U}$-globulin) used as an antigen may be naturally occurred ones (e.g., ones from tissue of liver, kidney, etc.), but may be recombinant proteins produced by a conventional gene engineering technique. Since the amino acid sequence or gene sequence of FABP has already been reported (Veerkamp and Maatman, Prog. Lipid Res., vol. 34, p. 17-52, 1995), a recombinant FABP can be prepared by gene engineering technique, for example, by designing a primer based on those reported data, cloning a cDNA from a suitable cDNA library by PCR (polymerase chain reaction), and using the cDNA thus obtained.

In addition, a fragment of FABP or a synthesized peptide having a partial sequence thereof can be used as an antigen, if necessary, after combining with a carrier of a high molecular substance (bovine serum albumin, hemocyanin, etc.).

The antibody specifically binding to FABP or $\alpha_{2U}$-globulin may be any antiserum, polyclonal antibody, monoclonal antibody, etc.

The antibody is preferably ones having high specificity, for example, when the antibody is an anti-L-FABP antibody, then the preferred is the one which substantially does not cross-react with H-FABP. In order to obtain an antibody having higher specificity, it is desirable to use a highly purified antigen.

In preparation of antibody, a warm-blooded animal is inoculated and immunized with a purified antigen (e.g., purified FABP, etc.) as prepared above. The immunized warm-blooded animal includes, for example, mammals (e.g., rabbit, sheep, rat, mouse, guinea pig, horse, pig, etc.), birds (e.g., chicken, duck, goose, etc.). When a rabbit is used, for example, about 100 μg to 1 mg of an antigen is emulsified in a physiological saline solution and Freund's complete adjuvant (about 1 ml), and the resultant is subcutaneously injected onto the back or the paw of the hinder leg of the rabbit. After the initial inoculation, the adjuvant is changed to a Freund's incomplete adjuvant, and then the rabbit is inoculated with the antigen 3 to 8 times every 2 to 4 weeks. The antigen is collected from a rabbit about 7 to 12 days after the final inoculation. When a mouse is used, the mouse is inoculated and immunized with an antigen at a dose of 10 to 30 μg/mouse subcutaneously, intraperitoneally or intravenously 3 to 8 times about every two weeks, and the antibody is collected from the mouse about 2 to 4 days after the final inoculation.

The polyclonal antibody can be prepared from the blood collected from the animals thus inoculated, by collecting the serum (antiserum), and then collecting IgG fractions therefrom. For example, the polyclonal IgG can be obtained by collecting IgG fractions from the antiserum by affinity chromatography using Protein G column.

The monoclonal antibody can be produced from hybridoma, which is obtained by fusing antibody-producing cells collected from the inoculated animals with immortalized cells. The immunized animal for monoclonal antibody is preferably a mouse or a rat. The production of hybridoma is carried out according to the method of Kohler & Milstein (Nature, vol. 256, p. 495-897, 1975), as follows. That is, antigen-producing cells (for example, spleen cells or lymph node cells, etc.) are collected from the animal immunized as mentioned above, which is subjected to cell fusion with suitable immortalized cells. The immortalized cells are preferably a cell line of myeloma cells (NSI-AG4/1, Sp2/O-Ag14, etc.). The myeloma cells are preferably non-secretors, which do not produce antibody or H-chain or L-chain of immunoglobulin, and have a selective marker, which can be used to distinguish between the non-fused myeloma cells and the fused hybridoma in a selective medium. For example, cell lines having 8-azaguanine-resistance (hipoxanthine-guanine-phosphoribosyl transferase deficiency), thymidine kinase deficiency, etc. as a selective marker are often used.

The cell fusion is carried out by adding a suitable fusion promoter such as polyethylene glycol. The cell fusion is preferably carried out at a ratio of about 10 antibody-producing cells per one immortalized cell, and at a cell density of about $10^6$ cells/ml of antibody-producing cells.

The fused cells are properly diluted, and incubated for 1 to 2 weeks in a selective medium. For example, when myeloma cells being resistant to 8-azaguanine are used and cultured in a medium containing HAT (hypoxanthine, aminopterin, thymidine), non-fused myeloma cells die and non-fused antibody-producing cells also die because the cell division cycle is restricted, but only fused cells can keep division and survive in a selective medium.

After cultivation in a selective medium, the existence of the desired antibody is detected, for example, by carrying out enzyme immunoassay for the culture supernatant thereof, and then it is subjected to cloning with limiting dilution method, by which the desired hybridoma being able to produce a monoclonal antibody recognizing the desired antigen can be selected. The selection of hybridoma is carried out so as to select a hybridoma (monoclonal antibody) having preferable properties in terms of antibody titer, class or subclass of antibody, affinity for antigen, specificity, epitope, etc. The IgG class of a monoclonal antibody is preferable.

The monoclonal antibody-producing hybridoma is implanted, for example, into the peritoneal of the immunized animal, and after a fixed term therefrom, ascites is collected from the animals, and the desired monoclonal antibody can be isolated therefrom. Alternatively, a hybridoma is cultured in a suitable medium for animal cell culture, and the desired monoclonal antibody can be isolated from the culture medium. Besides, when the desired hybridoma is isolated, then a gene encoding the desired monoclonal antibody is collected therefrom, and the desired monoclonal antibody can be expressed and produced in a suitable host by a conventional gene recombinant technique.

The purification isolation of antibody is carried out by a conventional purification method, such as ammonium sulfate precipitation, gel chromatography, ion exchange chromatography, affinity chromatography, or a combination thereof, if necessary.

Using the antibody thus obtained, FABP (or $\alpha_{2U}$-globulin) (antigen) in specimens can be detected by immunochemical assays.

When a specimen is a tissue section, the detection of antigen (FABP or $\alpha_{2U}$-globulin) is carried out by a conventional immunohisto staining. For example, a paraffin embedded section is prepared from the excised kidney tissue, and subjected to deparaffin, and fixed, and reacted with a primary antibody. The reaction mixture is washed, and reacted with a secondary antibody labeled with an enzyme such as peroxidase, and reacted with a coloring substrate, etc., and washed. Alternatively, the secondary reaction is carried out by using a biotinylated secondary antibody, and after the secondary reaction thereto are added a biotinylated enzyme and streptoavidin, and the mixture is reacted with a coloring substrate, etc.

When a specimen is urine, blood (or plasma or serum), or extract from kidney tissues, the detection and quantitative assay are carried out by a conventional radioimmunoassay (RIA), enzyme immunoassay (EIA), chemi-luminescence immunoassay, fluoroimmunoassay, etc. More particularly, a competitive method using an antibody and labeled antigen, a sandwich EIA using a combination of two kinds of monoclonal antibodies or polyclonal antibodies (or a combination of an monoclonal antibody and a polyclonal antibody) having a different recognition site for antigen, etc. are exemplified. In these assays, an antigen or an antibody may be fixed on a suitable carrier such as gel particles, cellulose particles, polyacrylamide gel, a physical absorbent (e.g., glass, styrene resin), if necessary. For example, a solid phase method is frequently utilized wherein an antigen or an antibody is fixed onto a solid phase such as polystyrene plate or beads. Further, a Western Blotting may be applied for detection.

In the above mentioned immunochemical assays, a labeled antigen or a labeled antibody may be used, if necessary. The labeling is carried out using in addition to radioisotopes (e.g., $^{124}$I, $^{14}$C, $^{3}$H), enzymes (e.g., peroxidase, alkaline phosphatase, etc.), luminescent substances (e.g., acridinium ester, isoluminol, luciferin, etc.), fluorescence substances (e.g., fluorescein isothiocyanate, etc.). Besides, a method using a combination of biotin labeling and streptoavidin is also utilized.

In addition to the above-mentioned immunochemical assays, for example, there is a convenient method wherein it is possible to detect FABP (or $\alpha_{2U}$-globulin) in specimens by using a fluorescent probe such as ANS (1-anilinonaphthalene-8-sulfonic acid), etc. as mentioned above and determining fatty acid binding activity as an indicator. However, since ANS strongly combines to albumin existing in large quantities in specimens of living body, certain specimens should be used for detection of FABP after pre-treatment of removing albumin therefrom.

When FABP is binding with fatty acid, the tertiary structure of FABP may somewhat differ from that of FABP not binding with fatty acid, so that the reactivity with antibodies may also differ. Besides, when FABP is binding with fatty acid, the binding property of FABP to fluorescent probe such as ANS may also differ from that of FABP not binding with fatty acid. Accordingly, especially in case the specimen will not be subjected to treatment with detergent or organic solvent, it may be necessary to consider the above-mentioned point since FABP in the specimen may exist in the form of binding with fatty acid.

The reagents for examination for the present examining method are, for example, anti-FABP antibody (antibody specifically binding to FABP) and labeled ones thereof, etc. The anti-FABP antibody includes, for example, anti-L-FABP antibody, anti-H-FABP antibody, anti-K-FABP antibody, etc., and anti-L-FABP antibody is especially preferable. The labeled antibody includes, for example, an antibody labeled with an enzyme such as peroxidase (enzyme-labeled antibody), an antibody labeled with biotin (biotinylated antibody), etc.

The kit for examination is, for example, ones wherein anti-FABP antibody is absorbed or bound onto a carrier such as beads and plate (96-well microplate, etc.). In addition, the kit may optionally contain other reagents necessary for EIA, etc., for example, enzyme-labeled secondary antibody, and a coloring substrate, etc.

The analysis of the results obtained by the present examination method is carried out as follows.

In the case that a specimen is from human or other animals excluding rodents, when the existing amount of L-FABP in the specimen collected from kidney tissues is lower than that of the normal kidney, then it is estimated that there is a high risk for bad prognosis, according to the degree thereof. Besides, since L-FABP exclusively exists at the proximal tubule, it will be desirable to focus on the existence of L-FABP especially at the proximal tubule.

On the other hand, in case the test result in urine is analyzed, generally, it is estimated that there is a high risk for bad prognosis when the existing level of L-FABP in the specimen is high, and it is estimated that prognosis is expected to be good when the existing level of L-FABP is low. The high level L-FABP in urine is considered to be explained by the leakage of L-FABP from the kidney (proximal tubule) into urine, so that the degree of the decrease of L-FABP in the kidney (proximal tubule) is reflected to the increase of the L-FABP in the urine.

However, in some individuals such as those having genetic mutation in the gene expression regulating system (e.g., maturity-onset type diabetes of young people: MODY), the L-FABP expression is originally low by nature. This kind of individuals can be distinguished, for example, as follows. That is, a suitable control marker, which is considered to be in parallel relation with the kidney tissue injury, is set up, and the amount of the control marker and the amount of L-FABP in urine of an individual suffering from renal disease are determined. When the amount of the control marker in urine is, for example, high but the amount of L-FABP is not high, it is estimated that the expression of L-FABP in this individual may be originally low and there is a high risk of bad prognosis.

When the existence of K-FABP in rat or mouse kidney tissues is lower than that of the normal kidney, then it is estimated that there is a high risk of bad prognosis, according to the degree thereof. Since K-FABP exclusively exists at the proximal tubule as well as L-FABP in human, it will be desirable to focus on the existence thereof especially at the proximal tubule. Further, when the amount of urinary $\alpha_{2U}$-globulin in male rat or mouse is lower than that of urine of a normal animal, it can be estimated that there is a high risk of bad prognosis.

When practicing the present method, a more precise diagnosis of the prognosis, etc. of kidney diseases can be carried out by comparing test results in a specimen with those of a control specimen. The control specimen includes, for example, a specimen collected from animals having normal kidneys, such as normal kidney tissues or urine.

Alternatively, it may be possible to compare the test results with those of a control specimen sampled from cases having the same kidney disease but showing different symptoms or different progresses, or from cases showing the same symptoms but at a different stage.

Further, it is also possible to calculate the further progress or to examine the effects of medication by comparing the test results of different specimens collected from the same case at different stages, and by examining the change with the lapse of time.

EXAMPLES

Example 1

Preparation (I) of Antibody Binding to FABP in Human Kidney Tissue (Preparation of Anti-Mouse FABP Antibody)

(1) Anti-Mouse L-FABP Polyclonal Antibody:

FABP existing at the human proximal tubule has been known to be mainly a liver-type FABP (L-FABP). Human L-FABP and mouse L-FABP have a high homology, and as an antibody binding to L-FABP in human kidney tissues, anti-mouse L-FABP antibody may be used.

Thus, an anti-mouse L-FABP polyclonal antibody was prepared. The antigen, mouse L-FABP, was prepared according to the method disclosed in the literature (Takahashi et al., Eur. J. Biochem., vol. 136, p. 589-601, 1983), as follows. That is, to the excised liver from a mouse killed by bleeding was added a four-time volume of 30 mM Tris-HCl buffer (pH 8), and the mixture was treated by a polythoron-type homogenizer. The resultant was centrifuged at 8000 rpm for 15 minutes, and the supernatant thus obtained was further ultracentrifuged at 100,000×g for 90 minutes to give the cytoplasm fraction. The cytoplasm fraction was separated by gel filtration column (SEPHACRYL™ S-100HR, manufactured by Pharmacia Inc.), and the fractions exhibiting a fatty acid binding activity were collected, checking as an indicator a binding activity to ANS (1-anilinonaphthalene-8-sulfonic acid, manufactured by Polysciences, Inc.). The obtained fractions of a molecular weight of 10 to 20 kilodalton were combined and dialyzed against 10 mM Tris-HCl buffer (pH 8.5), and then charged onto an anion exchange column (Hi-Trap Q, manufactured by Pharmacia Inc.) and eluted with a solvent of liner gradient to 500 mM NaCl, and the fractions exhibiting an ANS-binding activities were collected. Moreover, the resultant was further separated by gel filtration column (SEPHACRYL™ S-100HR, manufactured by Pharmacia Inc.) in the same manner as above, and each fraction thus obtained was subjected to SDS-polyacrylamide gel electrophoresis, and the fraction showing a single band of about 14 kilodalton was collected go give a purified mouse L-FABP.

The purified mouse-FABP obtained above was used as an antigen, and rabbits were immunized as mentioned below to give anti-mouse L-FABP antibody. That is, to the purified mouse L-FABP (200 µg/430 µl) was added Freund's complete adjuvant (470 µl), and the resultant emulsion was subcutaneously injected to rabbits on the back (5 points) and on the gaskin (4 points) in an amount of 100 µl each. Four weeks thereafter, the second immunization was carried out to the rabbits in the same amount except that the adjuvant was changed to Freund's incomplete adjuvant. Two weeks later, 100 µg thereof was injected, and then 50 µg thereof was injected another two weeks later, and the immunization was totally done four times. One week after the final immunization, the blood was collected from the heart, and the serum was separated to give an antiserum. The resulting antiserum was charged on HiTrap Protein G column (manufactured by Pharmacia Inc.), and the IgG fraction was isolated to give anti-mouse L-FABP polyclonal antibody (IgG). The Western Blotting was carried out using the anti-mouse L-FABP polyclonal antibody thus obtained, by which it was confirmed that the anti-mouse L-FABP polyclonal antibody can combine with the recombinant human L-FABP prepared in the same manner as in Example 2 mentioned below. Besides, the anti-mouse L-FABP polyclonal antibody did not cross-react with a purified mouse H-FABP.

(2) Anti-Mouse H-FABP Polyclonal Antibody:

It has been known that heart muscle-type FABP (H-FABP) exists at the human distal tubule. Since human H-FABP and mouse H-FABP have a high homology as well, anti-mouse H-FABP antibody may be used as an antibody binding to H-FABP in human kidney tissues. In the same manner as in the above (1), H-FABP was purified from mouse heart, and anti-mouse H-FABP polyclonal antibody (IgG) was obtained.

The Western Blotting was carried out using the resulting anti-mouse H-FABP polyclonal antibody, by which it was confirmed that the anti-mouse H-FABP polyclonal antibody can combine with mouse H-FABP, but did not cross-react with a purified mouse L-FABP and a recombinant human L-FABP.

Example 2

Preparation (II) of Antibody Binding to FABP in Human Kidney Tissues (Preparation of Anti-Human L-FABP Antibody)

(1) Purification of recombinant human L-FABP:

cDNA of human L-FABP was obtained by PCR (polymerase chain reaction) from the cDNA library derived from human liver (manufactured by CLONTECH Laboratories Inc., Cat # HL1115b Lot # 5621). An oligonucleotide of 23 to 27mers synthesized by a DNA synthesizer was used as a primer. The nucleotide sequence of the primer was designed based on the gene sequence of human L-FABP disclosed in the literature (Lowe et al., J. Biol. Chem., vol. 260, p. 3413-3417, 1985) and Gene Data Base (GENBANK Accession No. M10617), with adding a restriction enzyme recognition site for inserting an expression vector at the end of the primer. The obtained DNA fragment (about 420 base pairs) has a BamHI recognition site before the initiation codon, and the BamHI recognition site after the termination codon, and encodes the desired full-length human L-FABP.

The DNA fragment encoding human L-FABP obtained above was digested with a restriction enzyme BamHI, and inserted into the BamHI site of the fusion protein expression vector plasmid pMAL-cRI (manufactured by New England Biolabs) to give a plasmid pMAL/L-FABP for expression of recombinant human L-FABP fusion protein. In the pMAL/L-FABP, human L-FABP cDNA is inserted in proper direction following the junction sequence and the coding sequence of MBP (maltose binding protein) derived from the vector, and therefore the pMAL/L-FABP encodes the fusion protein consisting of MBP, the junction sequence and the human L-FABP.

The plasmid pMAL/L-FABP was introduced into a commercially available host cell *E. coli* JM109 strain (Yanisch-Perron C. et al., Gene, vol. 33, p. 103-119, 1985) (manufactured by TOYOBO CO., LTD.) for transformation, and the transformed strain, which became ampicillin-resistant, was cultured in LB medium to which was added IPTG (isopropyl-β-D-thigalalctoside) in mid course.

The obtained cells were broken by ultrasonic, and the cell extract was dialyzed against 5 mM Tris-HCl buffer (pH 8.5). The resultant was separated by anion exchange column (RE-SOURSE Q 6 ml, manufactured by Pharmacia, Inc.), eluted with a solvent of liner gradient to 300 mM NaCl, and the fraction showing ANS-binding activity was collected. The fraction was concentrated by ultra filtration with Centriprep (manufactured by AMICON LTD.), and separated by gel filtration column (SUPERDEX™ 75 pg, manufactured by Pharmacia Inc.), and the fraction showing ANS-binding activity was collected to give a human L-FABP fusion protein. To the human L-FABP fusion protein thus obtained was added Factor Xa (manufactured by New England Biolabs Inc.) in 1/100 weight, and the mixture was reacted at room temperature overnight for restriction degradation. The reaction solution after the enzyme treatment was separated again by gel filtration, and the fraction of about 14 kilodalton showing ANS-binding activity was collected to give a recombinant human L-FABP. The obtained purified protein was subjected to SDS-polyacrylamide gel electrophoresis, and subjected to silver staining, from which only one band was confirmed.

The purified recombinant human L-FABP thus obtained was assayed for amino acid sequence thereof by an amino acid sequencer. As a result, it was confirmed that there were 14 amino acid residues corresponding to the known N-terminus region of the human L-FABP, following the 6 amino acid residues (Ile Ser Glu Phe Gly Ser) (SEQ ID NO: 1) derived from the junction sequence of the vector at the N-terminus amino acid sequence thereof.

(2) Preparation of Anti-Human L-FABP Polyclonal Antibody:

Using as an antigen the purified recombinant human L-FABP as obtained in the above (1), rabbits were immunized in the same manner as in Example 1-(1), and anti-human L-FABP polyclonal antibody (IgG) was obtained from anti-human L-FABP antiserum.

Example 3

Localization of FABP in Human Kidney Tissues (Normal Kidney Tissues)

Normal human kidney tissues were subjected to immunohisto staining of FABP. The human kidney tissues were normal portions of the kidney excised from the patient with renal cancer. A primary antibody for L-FABP staining was the anti-mouse L-FABP polyclonal antibody (IgG) prepared in the same manner as in Example 1-(1). A primary antibody for H-FABP staining was the anti-mouse H-FABP polyclonal antibody (IgG) prepared in the same manner as in Example 1-(2). The immunostaining was carried out using Vectastain ABC kit (manufactured by Vector Laboratory, Inc.), and a secondary antibody was a biotinylated anti-rabbit IgG, and an enzyme was a biotinylated horseradish peroxidase, and a coloring substrate was DAB (3,3'-diaminobensidine tetrahydrochloride).

Figure 1B:
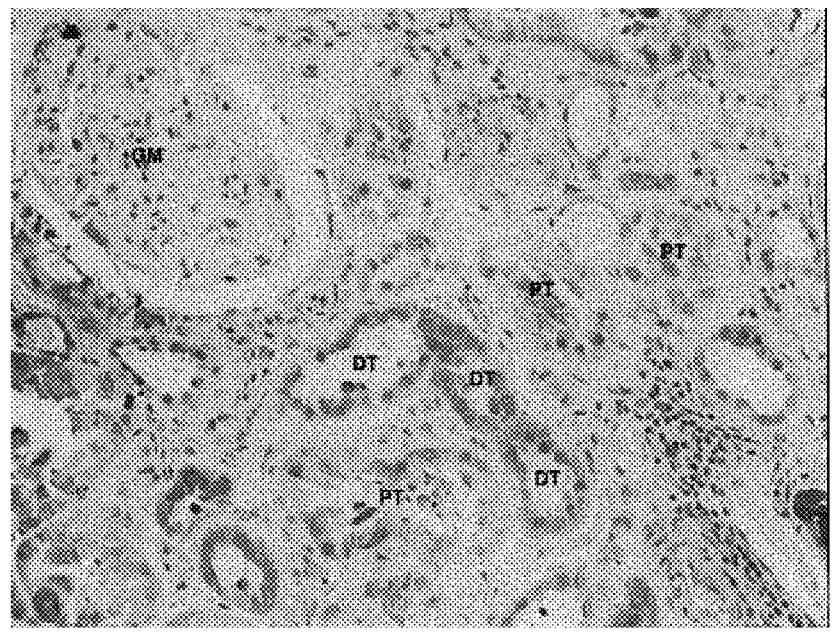

The results are shown in FIG. 1. When anti-L-FABP antibody was used, the proximal tubule was stained. On the other hand, when anti-H-FABP antibody was used, the distal tubule was mainly stained, and the proximal tubule was slightly stained as well. The glomerulus was not stained at all by either of antibodies.

As clear from the above, it was confirmed that in the normal kidney tissues, L-FABP exists at the proximal tubule, and H-FABP mainly exists at the distal tubule.

Example 4

Detection of FABP in Kidney Tissues of Patient of Kidney Disease

Kidney tissue samples were collected by kidney biopsy from two patients (Patient 1 and Patient 2) who had been diagnosed as IgA nephropathy and had shown a resistance against steroid-treatment, and the samples were subjected to L-FABP immunohisto staining. The prognosis of Patient 1 was bad, and developing into renal insufficiency 5 years after the renal biopsy, Patient 1 became in need of dialysis treatment. On the other hand, the prognosis of Patient 2 was good, and after the renal biopsy, Patient 2 was in remission.

Figure 2:
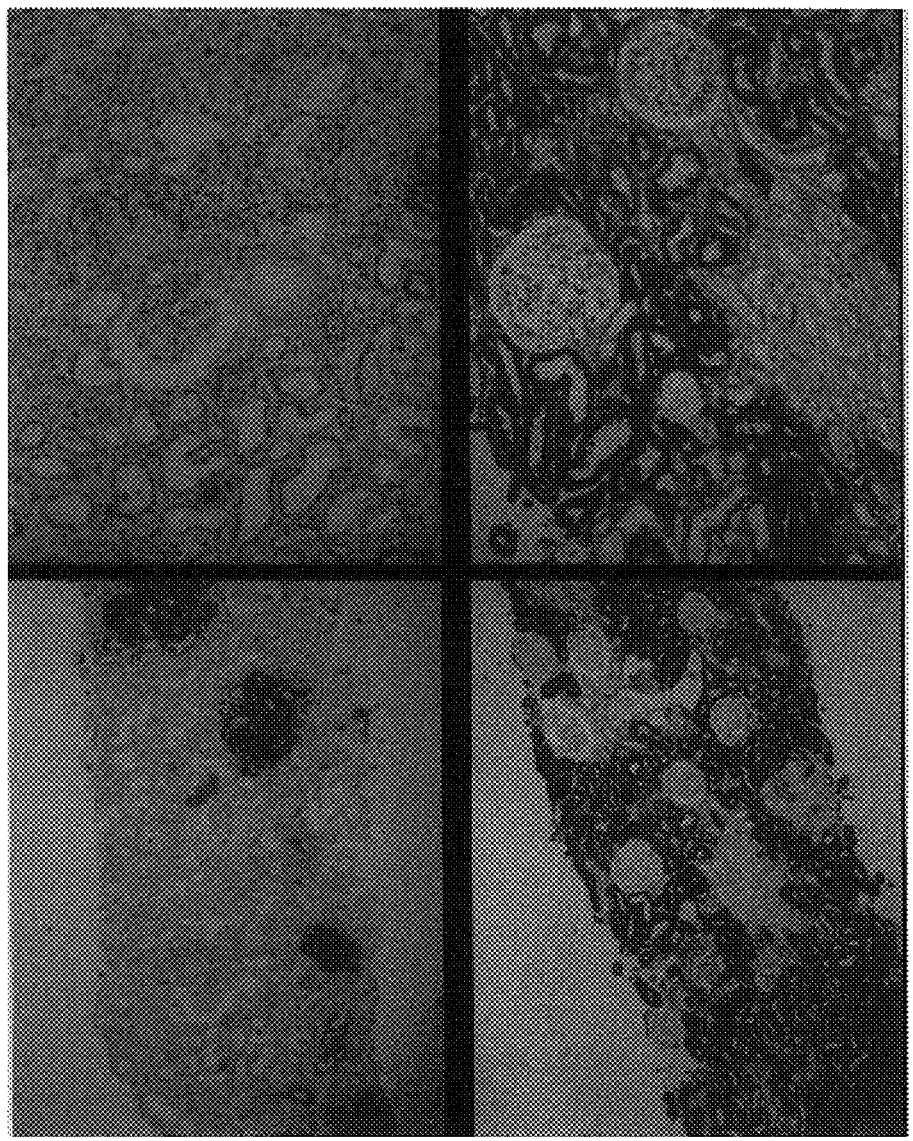
FIG. 2 is a photocopy of the tissue section, indicating the results of immunostaining of L-FABP in kidney tissue in a patient with IgA nephropathy.

The immunohisto staining was carried out using as a primary antibody anti-mouse L-FABP polyclonal antibody (IgG) in the same manner as in Example 3 mentioned above. The results are shown in FIG. 2. In the kidney tissues of Patient 2, the proximal tubule was overall stained, and the existence of L-FABP was confirmed. On the other hand, in the kidney tissues of Patient 1, the stainability was significantly reduced, and the existence of L-FABP was hardly observed.

From the above results, the existing amount of L-FABP in kidney tissues and the goodness of prognosis of kidney diseases correlate each other, and hence, by detecting L-FABP in kidney tissues, it is possible to diagnose a risk of bad prognosis of kidney diseases.

Example 5A

Detection of FABP in Urine of Patients with Kidney Disease

The amount of L-FABP leaked into urine was determined by Sandwich ELISA on urine specimens collected from 34 patients with kidney diseases, as follows. That is, anti-mouse L-FABP polyclonal antibody (IgG) was previously fixed on a plate, and thereto was added a urine specimen, and the plate was allowed to stand for a prescribed period, and washed. To the plate was added a biotinylated anti-mouse L-FABP polyclonal antibody (IgG), and washed, and the plate was detected with a commercially available avidin-biotin detection kit (manufactured by FUNAKOSHI, LTD., ABC-PO Kit), and the absorbance was determined.

In addition, the amount of NAG (N-acetyl-β-D-glucosaminidase) leaked into those urine specimens was also determined. NAG is a marker enzyme existing in kidney tissue cells, and the amount of NAG leaked into urine is generally considered as an indicator for kidney tissue injury. The amount of urinary NAG was determined according to the method disclosed in the literature (Nippon-Rinsho, vol. 43, the autumn extra edition, p. 234-236, 1985).

In order to analyze the results of each specimen, the data were plotted in a graph wherein the y-axis is the L-FABP amount and the x-axis is the NAG amount. As a result, it is confirmed that the leaked NAG amount and the leaked L-FABP amount positively correlate each other in standard cases. However, in a group consisting of some cases (about 5 typical cases), although the leaked NAG amount was high (i.e., the injury of tissues was massive), the leaked L-FABP amount was low. In this group, it is considered that the existence of L-FABP in kidney tissues is low, and hence, there is a high risk of bad prognosis in this group.

Example 5B

Detection of FABP in Urine of Patients with Kidney Disease (Prospective Study)

In the prospective study, patients of chronic renal disease were followed for a year. L-FABP in urine was determined by Sandwich ELISA using anti-L-FABP antibody. Urinary L-FABP (mg/g creatinine in urine) at the start point was greater in patients whose serum Cr (creatinine) was elevated during the period (i.e., progression patients) than in patients whose serum Cr remained stable (i.e., non-progression patients), while the serum Cr at the start point was in a similar level in both type of patients. In conclusion, urinary L-FABP is a reliable clinical marker for progression of chronic renal disease.

Example 6

Purification of FABP Derived from Rabbit Kidney Tissues

Rabbits were killed by bleeding, and the kidneys were excised therefrom, and FABP was purified in the same manner as in Example 1-(1) as mentioned above. That is, the excised kidneys were homogenized, and the cytoplasm fraction was obtained therefrom by centrifugation and ultracentrifugation. The cytoplasm was separated by gel filtration column (Superdex 75 pg, manufactured by Pharmacia Inc.), and the fractions of a molecular weight of 10 to 20 kilodalton showing ANS-binding activity were collected. The fractions were combined, and dialyzed against 30 mM Tris-HCl buffer (pH 7.5), and the resultant was eluted by anion exchange column (RESOURSE Q, manufactured by Pharmacia Inc.) (solvent; a liner gradient to 300 mM NaCl), and the fractions showing ANS-binding activity were collected as FABP. There were two peaks showing ANS-binding activity at 0 mM, and 60 mM of NaCl concentration.

Using the anti-mouse L-FABP antibody and the anti-mouse H-FABP antibody obtained in Example 1 mentioned above, the Western Blotting was carried out. From the results thereof, the protein contained in the peak at 0 mM of NaCl cross-reacted with anti-mouse L-FABP antibody, and it was considered as rabbit L-FABP. Further, the protein contained in the peak at 60 mM of NaCl cross-reacted with anti-mouse H-FABP, and it was considered as rabbit H-FABP. From these data, it was shown that at least two kinds of FABP, L-FABP and H-FABP, exist in rabbit kidney tissues, as in human kidney tissues.

Example 7

Analysis in Nephritis Model Mouse (1) Production of Nephritis Model Mouse:

An accelerated anti-GBM nephritis model mouse was produced according to the method disclosed in the literature (Nagai et al., Jpn. J. Pharmacol., vol. 32, p. 1117-1124, 1982), as follows. Rabbits were immunized with an antigen, mouse glomular basal membrane (GBM), to give antiserum (NTS: nephrotoxic serum). The obtained NTS was administered to a mouse to produce an anti-GBM nephritis model mouse. GBM was prepared according to the method disclosed in the literature (Nagai et al., Jpn. J. Pharmacol., vol. 32, p. 1117-1124, 1982).

Figure 3:
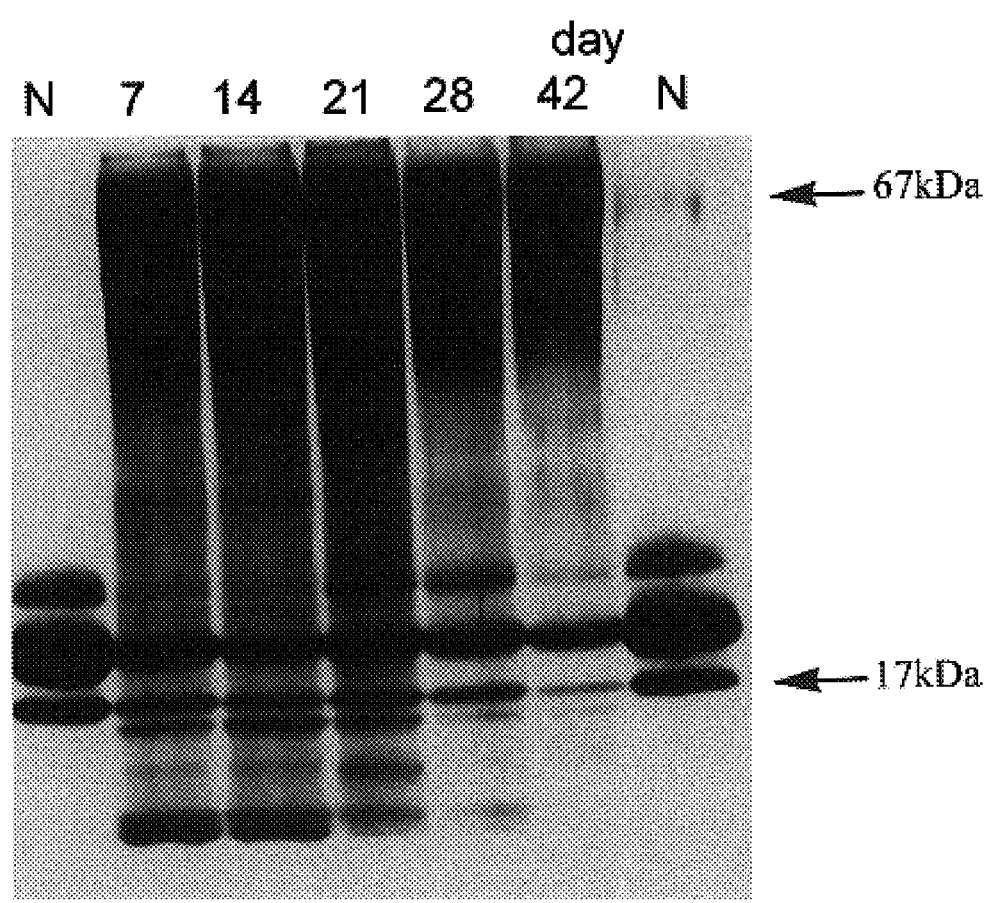
FIG. 3 is a photocopy of SDS-polyacrylamide gel electrophoresis, indicating the analysis results of urinary proteins in normal mice or mice with nephritis. In the drawings, N means the analysis results of normal mice, and 7, 14, 21, 28, 42 means days after the NTS-treatment in nephritis model mice.

(2) Analysis of Urinary Proteins of Nephritis Model Mouse:

The urine specimens of the accelerated anti-GBM nephritis model mouse as produced in the above (1) and a normal mouse were subjected to SDS-polyacrylamide gel electrophoresis, and subjected to silver staining, and the urinary proteins therein were compared. The results are shown in FIG. 3. In the nephritis model mouse, many strong bands of proteins including a main band (which was considered to be albumin) of molecular weight of about 67 kilodalton were observed even 7 days after the NTS-treatment, and the symptom of so-called elevated proteinuria was observed. On the other hand, there was observed a clear band of about 17 kilodalton in the normal mouse, while such a band was remarkably reduced in the nephritis model mouse.

Most of urinary proteins are serum proteins leaked into urine through the barrier of glomular basal membrane. However, like the protein mentioned above, from the fact that the amount in urine is reduced in the elevated proteinuria than in the normal urine, it is considered that said protein is not a mere leaked protein but may play a specific role in the relation with the renal function disorder.

Said protein of about 17 kilodalton was purified and isolated as follows. That is, the sampled urine was subjected to SDS-polyacrylamide gel electrophoresis, and stained with Coomassie Brilliant Blue, and the band of about 17 kilodalton was cut off from the gel. The gel section thus obtained was put into a dialysis membrane. The gel section was subjected to electrophoresis by a leveled electrophoresis apparatus until the stained band was completely dropped off from the gel. The eluate was collected and concentrated by ultrafiltration.

The obtained purified protein was assayed using an amino acid sequencer, and the amino acid sequence at the N-terminus thereof was determined. Based on the determined 15 amino acid sequence, the homology search was carried out with the amino acid sequence of known proteins, by which it was confirmed that the protein thus obtained was homologous with the $\alpha_{2U}$-globulin (called Major Urinary Protein as well) (Data base name: SWISS-PROT, Accession No.: P02762).

The $\alpha_{2U}$-globulin has been known as a main urinary protein being specific to male rats and mice. The $\alpha_{2U}$-globulin is synthesized in the liver, and released into the blood, and excreted into urine via the kidney, and it is considered that during the above process, a part of the $\alpha_{2U}$-globulin is reabsorbed into the urinary tubule of the kidney, and converted into a kidney-type FABP (K-FABP) by processing within the cells.

(3) Detection of FABP (K-FABP) in Kidney Tissues of Nephritis Model Mouse:

In the accelerated GBM nephritis model mouse, the relation between the increased or decreased amount of K-FABP in kidney tissues and the kidney tissue injury was analyzed by immunohisto staining.

It is known that at least the 9 amino acid residues at the N-terminus of $\alpha_{2U}$-globulin (180 amino acid residues, about 20 kilodalton) were deleted and became K-FABP (about 15 kilodalton) in rats.

As an antibody for K-FABP immunostaining, a commercially available goat anti-mouse $\alpha_{2U}$-globulin antiserum (manufactured by Nordick Inc., Anti Major Urinary Protein Ab) was used.

The immunohisto staining of K-FABP in the kidney tissues was carried out using Vectastain ABC Kit (manufactured by Vector Laboratory, Inc.), as follows. That is, a kidney paraffin section of thickness of 3 µm was prepared from the mouse kidney, and subjected to deparaffin. The resultant was lightly washed with a physiological saline solution containing 0.05% Tween 20 (pH 7.4) (hereinafter, referred to as PBST), and fixed in methanol containing 0.5% hydrogen peroxide for 30 minutes, and washed lightly with PBST, and subjected to marking. The resultant was washed twice with PBST for 5 minutes each, and blocked in a PBS containing a normal goat serum for 60 minutes, and then reacted in a PBS containing as a primary antibody anti-mouse $\alpha_{2U}$-globulin antiserum overnight. The result was washed thrice with PBST for 5 minutes each (hereinafter, the same), and reacted in a PBS containing as a secondary antibody biotinylated anti-rabbit IgG antibody (manufactured by Vector Laboratory Inc.) for 45 minutes. The resultant was further washed with PBST, and reacted in a solution containing streptoavidin and biotinylated peroxidase (manufactured by Vector Laboratory Inc.) for 45 minutes, and washed again with PBST, and then put in a PBST containing a coloring substrate DAB and $H_2O_2$ for coloring. The coloring procedure was checked with a microscope, and properly quenched by washing with distilled water.

The tissue section thus immunostained as mentioned above was further stained with hematoxylin, and the nucleus was stained. The resultant was washed with distilled water, and subjected to dehydration, penetration and mounting by a conventional method.

Azan staining for collagen fiber was carried out on the mouse kidney paraffin section prepared in the same manner as in the above, according to the method disclosed in the literature (Ishikawa et al., Medical Technology, vol. 19, p. 176-177, 1991), as follows. That is, after the deparaffin of the paraffin embedded section, the section was mordanted in a mixture of 10% potassium chromate and 10% trichloroacetic acid in equivolume for 20 minutes, and washed with distilled water for 5 minutes. The resultant was soaked in 0.8% Orange G aqueous solution for 10 minutes, washed with distilled water for about 10 seconds (hereinafter, the same), and soaked in an Azocarmine G solution for 60 minutes. Then, the resultant was further washed with distilled water, soaked in a solution of aniline alcohol for 3 seconds, and fractionated. The resultant was washed with distilled water, treated with acetic alcohol for one minute, washed with distilled water, and further treated with 2.5% phosphowolframic acid solution for 20 minutes. The resultant was further washed with distilled water, and stained in a mixture of Aniline Blue/Orange G for 20-60 minutes while the resultant was continuatively checked by microscope. After staining, the resultant was subjected to dehydration, penetration and mounting.

Figure 4A:
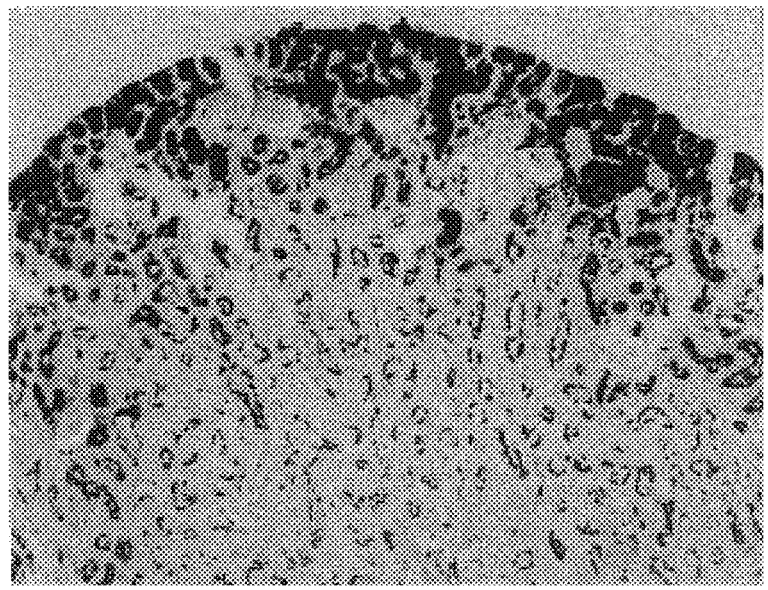
FIG. 4 is a photocopy of the tissue section, indicating the results of immunostaining of K-FABP in kidney tissues of normal mice and nephritis mice. Drawing A shows the tissue section of normal mice, and Drawing B shows the tissue section of the nephritis model mice at the 42nd day after the NTS-treatment.
Figure 4B:
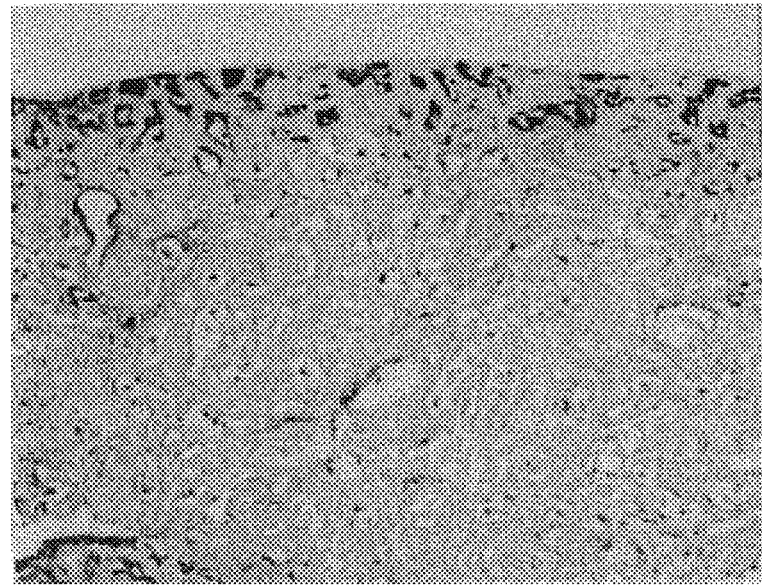

In the same manner as in the above (1) and (2), the kidney tissue sections of the accelerated anti-GBM nephritis model mouse and the normal mouse, in which the urinary proteins were analyzed, were subjected to K-FABP immunostaining. The results are shown in FIG. 4, and from the results, it was confirmed that there was a protein being recognized by anti-$\alpha_{2U}$-globulin antibody at the proximal tubule of the normal mouse kidney tissue, and this protein was considered as K-FABP derived from the $\alpha_{2U}$-globulin. On the other hand, in the mouse 42 days after the NTS-treatment, in which the amount of $\alpha_{2U}$-globulin in urine was decreased, the amount of K-FABP at the proximal tubule of kidney tissue was remarkably reduced as compared with that of the normal mouse.

In addition, when the kidney tissue sections same as above were subjected to Azan staining in order to check how far the interstitium was fiberosed, fiberosed part was very little in the mouse 42 days after the NTS-treatment, wherein the K-FABP reduction was confirmed in the proximal tubule, but the fiberosed part was significantly expanded in the mouse 84 days after the NTS-treatment.

From the above results, it was understood that the reduction of the urinary $\alpha_{2U}$-globulin amount, and the reduction of the K-FABP amount in kidney tissues occurred prior to the interstitial fibrosis, and therefore, they can be an indicator for diagnosing the prognosis of kidney diseases.

Further, since the K-FABP amount was also decreased in the nephritis mouse wherein the urinary $\alpha_{2U}$-globulin amount was decreased, it was considered that the reduction of the urinary $\alpha_{2U}$-globulin amount was not due to the exaltation of the reabsorption thereof at the proximal tubule, but the production of the $\alpha_{2U}$-globulin at the liver per se was inhibited.

INDUSTRIAL APPLICABILITY

According to the present method, it is possible to obtain test results which may be very important information for diagnosis of prognosis of kidney diseases, that has been very difficult in the past. Based on test results obtained by the present method, it may be possible to select a suitable method for treatment of diseases with taking into consideration risks as to the prognosis, etc. Besides, the present method can be applied to, in addition to the kidney tissue samples, urine samples as well, so that the examination procedure can be simple and efficient.

---

---

The invention claimed is:

1. A method for diagnosis or prognosis of a kidney disease in human, which comprises the steps of:
   (a) preparing a specimen collected from a human;
   (b) detecting liver-type fatty acid binding protein contained in said specimen; and
   (c) diagnosing or prognosing the kidney disease based on the test result of the detection in (b), wherein said specimen is kidney tissue or urine.

2. The method according to claim 1, wherein the specimen is urine.

3. The method according to claim 2, wherein the liver-type fatty acid binding protein is derived from kidney tissue.

4. The method according to claim 2, which further comprises a step of comparing the test result with that of a control specimen, said control specimen being collected from a human having normal kidney tissue, or collected from a human having the same kidney disease but showing different symptoms or different progress.

5. The method according to claim 2, wherein the step (b) is carried out by (i) contacting the specimen with an antibody specifically binding to liver-type fatty acid binding protein;
(ii) separating unbound antibody from the antibody bound to said protein; and
(iii) detecting the antibody bound to said protein.

6. The method according to claim 5, wherein the antibody specifically binding to the liver-type fatty acid binding protein is an antibody that does not cross-react with a heart muscle-type fatty acid binding protein.

7. The method according to claim 2, wherein the existing level of liver-type fatty acid binding protein in the specimen is diagnostic or prognostic of the kidney disease.

8. The method according to claim 2, which further comprises the step of comparing the test result of the specimen with a different specimen collected from the same human at different stage, and examining the change with the lapse of time.

9. The method according to claim 2, wherein the kidney disease is a chronic renal disease.

10. The method according to claim 2, wherein the kidney disease is a disease selected from the group consisting of diabetic nephropathy, glomerulonephritis, nephrotic syndrome, focal glomerulosclerosis, immune complex nephropathy, lupus nephritis, drug-induced renal injury, renal insufficiency and kidney graft rejection.

11. The method according to claim 10, wherein the immune complex nephropathy is selected from the group consisting of IgA nephropathy and membranous nephropathy.

12. A method for diagnosing the progression of kidney disease in a patient suffering therefrom, comprising the steps of:
(a) preparing a specimen collected from said patient;
(b) assaying for liver-type fatty acid binding protein contained in said specimen; and
(c) diagnosing the progression of the kidney disease based on the test result of the detection in (b), wherein said specimen is kidney tissue or urine.

13. The method according to claim 12, wherein the specimen is urine.

* * * * *

UNITED STATES PATENT AND TRADEMARK OFFICE
CERTIFICATE OF CORRECTION

| | |
|---|---|
| PATENT NO. | : 7,592,148 B1 |
| APPLICATION NO. | : 09/578693 |
| DATED | : September 22, 2009 |
| INVENTOR(S) | : Masaya Yamanouchi et al. |

It is certified that error appears in the above-identified patent and that said Letters Patent is hereby corrected as shown below:

On the front page of the Letters Patent, the filing date is incorrect:

"(22) Filed: July 26, 2000"

should read

--(22) Filed: May 26, 2000--

Signed and Sealed this

Twenty-ninth Day of June, 2010

David J. Kappos
*Director of the United States Patent and Trademark Office*

SEQUENCE LISTING

```
<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Ile Ser Glu Phe Gly Ser
1               5
```